United States Patent
Avery et al.

(10) Patent No.: US 6,596,492 B2
(45) Date of Patent: Jul. 22, 2003

(54) PCR MATERIALS AND METHODS USEFUL TO DETECT CANINE AND FELINE LYMPHOID MALIGNANCIES

(75) Inventors: Anne C. Avery, Fort Collins, CO (US); Robert Burnett, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/903,413

(22) Filed: Jul. 10, 2001

(65) Prior Publication Data

US 2002/0160373 A1 Oct. 31, 2002

Related U.S. Application Data (60) Provisional application No. 60/217,611, filed on Jul. 11, 2000.

(51) Int. Cl.$^7$ ............................. C12Q 1/68; C12P 19/34
(52) U.S. Cl. .......................................... 435/6; 435/91.2
(58) Field of Search ............................ 435/6, 91.2, 810

(56) References Cited

U.S. PATENT DOCUMENTS

| | | | | |
|---|---|---|---|---|
| 5,296,351 A | | 3/1994 | Morley et al. .................. | 435/6 |
| 5,418,134 A | | 5/1995 | Morley et al. .................. | 435/6 |
| 5,635,354 A | * | 6/1997 | Kourilsky et al. ............. | 435/6 |
| 6,030,830 A | * | 2/2000 | Saxon et al. ............. | 435/320.1 |
| 6,087,096 A | * | 7/2000 | Dau et al. ....................... | 435/6 |
| 6,416,948 B1 | * | 7/2002 | Pilarski | |

OTHER PUBLICATIONS

Avery, A. and Burnett, R.C., Canine TCR gamma V–J junction, GenBank Accession AF079118 (Jul. 20, 1998).
Avery, A. and Burnett, R.C., Canine TCR gamma V–J junction, GenBank Accession AF079119 (Jul. 20, 1998).
Avery, A. and Burnett, R.C., Canine TCR gamma V–J junction, GenBank Accession AF079120 (Jul. 20, 1998).
Avery, A. and Burnett, R.C., Canine TCR gamma V–J junction, GenBank Accession AF079121 (Jul. 20, 1998).
Avery, A. and Burnett, R.C., Canine TCR gamma V–J junction, GenBank Accession AF079122 (Jul. 20, 1998).
Avery, A. and Burnett, R.C., Canine TCR gamma V–J junction, GenBank Accession AF079123 (Jul. 20, 1998).
Diss et al., "The polymerase chain reaction in the demonstration of monoclonality in T cell lymphomas" (1995) J. Clin. Pathol. 48:1045–1050.
Kyyoda et al., "Prognostic significance of immunoglobulin heavy chain gene rearrangement in patients with acute myelogenous leukemia" (1997) Leukemia 11:803–806.
Moore et al., "The use of immunological reagents in defining the pathogenesis of canine skin diseases involving proliferation of leukocytes" (1998) Adv Vet Derm 3:77–94.
Ruslander et al., "Immunophenotypic characterization of canine lymphoproliferative disorders" (1997) In Vivo 11:169–172.
Theodorou et al., "VJ rearrangements of the TCR γ locus in peripheral T–cell lymphomas: Analysis by polymerase chain reaction and denaturing gradient gel electrophoresis" (1996) J. Path. 178:303–310.
Theodorou et al., "Recombinanation pattern of the TCR γ locus in human peripheral T–Cell lymphomas" (1994) J. Path. 174:233–242.

* cited by examiner

Primary Examiner—Kenneth R. Horlick
(74) Attorney, Agent, or Firm—Greenlee Winner and Sullivan PC (57) ABSTRACT

The present invention provides materials and methods useful to diagnose B-cell and T-cell lymphoid malignancies in dogs and cats, as well as materials and methods useful to detect clonal expansion of certain populations of lymphoid cells using polymerase chain reaction. Primers useful for the methods include canine IgH CDR3-specific and caninen T-cell receptor gamma-specific primers.

22 Claims, 3 Drawing Sheets

PCR MATERIALS AND METHODS USEFUL TO DETECT CANINE AND FELINE LYMPHOID MALIGNANCIES

CROSS REFERENCE TO RELATED APPLICATIONS

This application claims benefit of U.S. Provisional Patent application No. 60/217,611, entitled "PCR Materials and Methods Useful to Detect Canine and Feline Lymphoid Malignancies," filed Jul. 11, 2000. The entire disclosure and contents of the above application is hereby incorporated by reference.

GOVERNMENT INTEREST STATEMENT

This invention was developed with funding from the National Institutes of Health, Grant Numbers AI42354, R01; AI26904, R01. The U.S. Government may have certain rights in this invention.

FIELD OF THE INVENTION

The present invention relates to the identification of clonal populations of canine T and B-cells that correlate with canine and/or feline lymphoma, and more particularly to the use of PCR to amplify certain clonal rearrangements that correlate with lymphoma.

BACKGROUND OF THE INVENTION

Polymerase chain reaction (PCR) has been used for amplification of DNA for over a decade. It is a well-characterized tool that has been shown to be useful in many assays, including clonal expansion-related assays. Various PCR assays have been developed by correlating unique primers with a disease state, or by identifying conditions that are uniquely capable of high levels of amplification.

In the past, canine and feline lymphomas have been identified by fairly inconclusive means, including physical examination, histology and cytology. Moreover, typical procedures currently used for obtaining sufficient material are invasive and expensive.

Thus, a need exists for less invasive and inexpensive diagnostic methods for identifying such lymphomas. The present invention satisfies this need and provides related advantages as well.

SUMMARY OF THE INVENTION

The present invention generally provides methods for detecting canine or feline clonal rearrangement. The present invention further relates to correlating such clonal rearrangements to a diagnosis of T-cell lymphoid malignancies in canids and felids or B-cell lymphoid malignancies in canids.

Accordingly, one aspect of the present invention is directed to a method of detecting clonal rearrangement in a test sample, comprising:

(a) conducting polymerase chain reaction using starting materials which comprise a test sample and at least one set of primers having at least one forward and at least one reverse primer, wherein the set of primers is selected from the group consisting of canine IgH CDR3-specific primers and canine T cell receptor gamma-specific primers; and (b) detecting clonal rearrangement in the test sample in the event one or more dominant and discrete DNA polymerase chain reaction products are present.

According to another aspect of the invention, a method to diagnose lymphoid malignancy in a canid or felid, comprising:

(a) obtaining a test sample from the canid or felid;

(b) conducting polymerase chain reaction using starting materials which comprise the test sample and at least one set of primers having at least one forward and at least one reverse primer, wherein the set of primers is selected from the group consisting of canine IgH CDR3-specific primers and canine T cell receptor gamma-specific primers; and (c) detecting clonal rearrangement in the test sample in the event one or more dominant and discrete DNA polymerase chain reaction products are present, wherein the presence of said DNA polymerase chain reaction products is diagnostic of lymphoid malignancy in the canid or felid.

Particularly useful primers for use in the above methods include, for example, those identified herein as SEQ.ID.NO:1, SEQ.ID.NO:2, SEQ.ID.NO:3, SEQ.ID.NO:4, SEQ.ID.NO:5, and SEQ.ID.NO:6. More specifically, useful forward primers include SEQ.ID.NO:1 and SEQ.ID.NO:6, while useful reverse primers include SEQ.ID.NO:2, SEQ.ID.NO:3, SEQ.ID.NO:4 and SEQ.ID.NO:5.

In addition, various techniques for detecting clonal rearrangment can be used, including, for example, gel electrophoresis, HPLC and other means known to those skilled in the art.

The above methods can be used to detect canine or feline T-cell clonal rearrangements and to diagnose canine or feline T-cell lymphoid malignancies by using canine T-cell receptor gamma-specific primers, including, for example, those identified as SEQ.ID.NO:4, SEQ.ID.NO:5 and SEQ.ID.NO:6.

Similarly, the above methods can be used to detect canine B-cell clonal rearrangements and to diagnose canine B-cell lymphoid malignancies by using canine IgH CDR3-specific primers, including, for example, those identified as SEQ.ID.NO:1, SEQ.ID.NO:2, and SEQ.ID.NO:3.

The present methods can also be used to distinguish between T-cell lymphomas and B-cell lymphomas in which canine IgH CDR-specific primers and canine T-cell receptor gamma-specific primers are used in the methods and detecting the presence of any PCR products obtained.

In a further aspect of the invention, kits containing desired starting materials and associated components for performing the methods described herein are also provided. Other objects and features of the present invention will be apparent from the following detailed description of the invention.

BRIEF DESCRIPTION OF THE DRAWINGS

FIG. 1A. shows DNA from normal, non-lymphoid tissue, such as liver, contains no rearranged immunoglobulin genes. PCR primers placed at the locations that are indicated by the arrows would amplify no product, because the germline distance between the V and J segments is several kilobases (too long for a standard PCR reaction). FIG. 1B shows recombination brings together V, D and J genes to form the gene that encodes the complementarity-determining region 3 of the antibody molecule. The joining site between V, D and J genes varies with each rearrangement. In addition, nucleotides can be added to the junctions between each gene (indicated by black boxes). PCR amplification using primers at the designated sites would amplify products of varying sizes, which would result in a smear when separated by size using PAGE. FIG. 1C shows that when the amplified DNA is from neoplastic tissue, a single length product predominates. Each lane represents a different neoplasm, indicating that each neoplasm would have a PCR product of a unique size. Hypothetical amplifications of three different neoplasms are shown.

FIGS. 3A–3D provide an analysis of samples using primers for Ig major (Dp-1 and Dp-2) (FIG. 3A), Dp-1 and Dp-3v2 (FIG. 3B), TCRγ (FIG. 3C) and the Cmu primers (FIG. 3D) as positive control. Lanes are numbered starting with the first sample, so the negative control isn't counted. Lanes 8 and 9 in FIG. 3A, and 13 and 14 in FIG. 3C were photographically enhanced because they were dim controls for DNA. All the samples that were amplified with a single primer pair were run on the same gel and compared to the other samples on the gel. Fifteen samples are shown analyzed with each of the three primer pairs. The DNA analyzed was derived from the following sources (lane #—sample source—diagnosis); 1—bm—lymphoblastic leukemia, 2—biopsy—lymphoma, 3—peritoneal fluid—lymphoma, 4—blood—lymphocytic leukemia, 5—biopsy—lymphoma, 6—l.n. aspirate—lymphoma, 7—blood—lymphocytic leukemia, 8—b.m.—lymphoma, 9—pleural fluid—lymphoma, 10—cerebrospinal fluid—lymphoma, 11—b.m.—lymphoma (same dog as 10), 12—b.m.—lymphoma, 13—blood—lymphoma, 14—blood—lymphoma, 15—blood—lymphocytic leukemia.

FIG. 2A: DNA from a neoplastic sample was mixed with DNA from the indicated tissue in the amounts shown. PCR for Ig rearrangement was carried out as described on the mixed samples. FIG. 2B: similar to FIG. 2A, except that PCR for TCR was used. M represents the molecular weight markers.

DETAILED DESCRIPTION OF THE INVENTION

The present invention provides novel PCR methods correlating unique primers with lymphomas. The invention provides objective methods for diagnosing T-cell in dogs and cats and/or B-cell lymphoma in dogs, assays for determining the stage of lymphoma, assays informative for follow-up care, and generally, the detection of clonal expansion of B or T cells in dogs or cats, whether the expansion is due to neoplasm or not.

Certain terms used to describe the present invention are defined below. Where the definition of terms departs from the commonly used meaning of the term, each term is intended to defined as provided below, unless specifically indicated.

For the purposes of the present invention, the term "amplicon(s)" refers to a nucleic acid(s) produced through use of primers in PCR.

For the purposes of the present invention, the term "canine IgH CDR3-specific primers" refers to primers capable of amplifying a detectable PCR product from the CDR3 region of canine IgH of at least 45 base pairs, but not longer than 200 base pairs.

For the purposes of the present invention, the term "canine T cell receptor gamma-specific primers" refers to primers capable of amplifying a detectable PCR product from the canine and/or feline T cell receptor gamma of at least 45 base pairs, but not longer than 200 base pairs.

For the purposes of the present invention, the term "discrete DNA polymerase chain reaction products" refers to any DNA polymerase chain reaction products which are neither a smear on a gel, or undetectable by known or developed means.

For the purposes of the present invention, the term "dominant DNA polymerase chain reaction products" refers to any DNA polymerase chain reaction products which are identifiable and are not a DNA ladder of similarly-abundant products, although a ladder may sometimes contain a dominant DNA polymerase chain reaction product or products.

For the purposes of the present invention, the term "set of primers" means at least one forward and at least one reverse primer, that, when used in a PCR assay in appropriate amounts, is capable of producing an amplicon.

The present invention is generally directed to methods of detecting clonal rearrangement in a test sample. Such methods are accomplished by:
(a) conducting polymerase chain reaction using starting materials which comprise a test sample and at least one set of primers having at least one forward and at least one reverse primer, wherein the set of primers is selected from the group consisting of canine IgH CDR3-specific primers and canine T cell receptor gamma-specific primers; and
(b) detecting clonal rearrangement in the test sample in the event one or more dominant and discrete DNA polymerase chain reaction products are present.

In the methods disclosed herein, including the general method described above and more specific methods described below, the detection of clonal rearrangement of step (b) can be accomplished by any means known in the art, including for example, by gel electrophoresis or by size separation techniques.

In addition, primers useful in the methods described herein can be derived from canine IgH CDR3 and T-cell receptor gamma in accordance with the guidance provided herein and by means known in the art. Particularly useful forward primers include the primers having sequences identified as SEQ.ID.NO: 1 and SEQ.ID.NO:6, while particularly useful reverse primers include the primers having sequences identified as SEQ.ID.NO:2, SEQ.ID.NO:3, SEQ.ID.NO:4, and SEQ.ID.NO:5. Any combination of forward and reverse primers selected from cannine IgH CDR3-specific primers and/or canine T-cell receptor gamma-specifi primers are contemplated for use in the present methods. However, particularly useful sets of forward and reverse primers include: (i) SEQ.ID.NO:1 and SEQ.ID.NO:2; (ii) SEQ.ID.NO:1 and SEQ.ID.NO:3; (iii) SEQ.ID.NO:6 and SEQ.ID.NO:4; and (iv) SEQ.ID.NO:6 and SEQ.ID.NO:5.

The above general method for detecting clonal rearrangement in a test sample can be used to diagnose canine or feline lymphoid malignancy. The presence of such lymphoid malignancy is correlated with the presence of one or more dominant and discrete DNA polymerase chain reaction product present in the test sample. Accordingly, methods to diagnose canine or feline lympid malignancy in a canid or felid is accomplished by:
(a) obtaining a test sample from the canid or felid;
(b) conducting polymerase chain reaction using starting materials which comprise the test sample and at least one set of primers having at least one forward and at least one reverse primer, wherein the set of primers is selected from the group consisting of canine IgH CDR3-specific primers and canine T cell receptor gamma-specific primers; and
(c) detecting clonal rearrangement in the test sample in the event one or more dominant and discrete DNA polymerase chain reaction products are present, wherein the presence of said DNA polymerase chain reaction products is diagnostic of lymphoid malignancy in the canid or felid.

The above methods can be used to specifically detect canine or feline T-cell clonal rearrangements and to diagnose canine or feline T-cell lymphoid malignancies by using canine T-cell receptor gamma-specific primers. The methods for detecting canine or feline T-cell clonal rearrangements in a test sample can be accomplished by:

(a) conducting polymerase chain reaction using starting materials which comprise a test sample and at least one set of primers having at least one forward and at least one reverse primer, wherein the set of primers is selected from the group consisting of canine T cell receptor gamma-specific primers; and (b) detecting clonal rearrangement in the test sample in the event one or more dominant and discrete DNA polymerase chain reaction products are present.

Methods of diagnosing canine or feline T-cell lymphoid malignancy in a canid or felid can be accomplished by:

(a) obtaining a test sample from the canid or felid;

(b) conducting polymerase chain reaction using starting materials which comprise the test sample and at least one set of primers having at least one forward and at least one reverse primer, wherein the set of primers is selected from the group consisting of canine T cell receptor gamma-specific primers; and (c) detecting clonal rearrangement in the test sample in the event one or more dominant and discrete DNA polymerase chain reaction products are present, wherein the presence of said DNA polymerase chain reaction products is diagnostic of T-cell lymphoid malignancy in the canid or felid.

In the methods for detecting T-cell clonal rearrangement and diagnosing T-cell lymphoid malignancy, T-cell receptor gamma-specific primers that correlate with clonal rearrangments indicative of T-cell lymphomas can be used. Those skilled in the art can readily identify useful canine T-cell receptor gamma-specific primers using the guidance provided herein and techniques known to them. Particularly useful primers include primers having sequences identified as SEQ.ID.NO:4, SEQ.ID.NO:5 and SEQ.ID.NO:6. Particularly useful sets of primers include SEQ.ID.NO:6 as the forward primer and SEQ.ID.NO:4 or SEQ.ID.NO:5 as the reverse primer.

Similarly, the above general methods can be used to detect canine B-cell clonal rearrangements and to diagnose canine B-cell lymphoid malignancies by using canine IgH CDR3-specific primers. The methods for detecting canine B-cell clonal rearrangements in a test sample can be accomplished by:

(a) conducting polymerase chain reaction using starting materials which comprise a test sample and at least one set of primers having at least one forward and at least one reverse primer, wherein the set of primers is selected from the group consisting of canine IgH CDR3-specific primers; and (b) detecting clonal rearrangement in the test sample in the event one or more dominant and discrete DNA polymerase chain reaction products are present.

Methods of diagnosing B-cell lymphoid malignancy in a canid can be accomplished by:

(a) obtaining a test sample from the canid;

(b) conducting a polymerase chain reaction using starting materials which comprise the test sample and at least one set of primers having at least one forward and at least one reverse primer, wherein the set of primers is selected from the group consisting of canine IgH CDR3-specific primers; and (c) detecting clonal rearrangement in the test sample in the event one or more dominant and discrete DNA polymerase chain reaction products are present, wherein the presence of said DNA polymerase chain reaction products is diagnostic of B-cell lymphoid malignancy in the canid.

In the specific methods for detecting B-cell clonal rearrangement and diagnosing B-cell lymphoid malignancy, any IgH CDR3-specific primers that correlate with clonal rearrangments indicative of B-cell lymphomas can be used. Those skilled in the art can readily identify useful canine IgH CDR3-specific primers using the guidance provided herein and techniques known to them. Particularly useful primers include primers having sequences identified as SEQ.ID.NO: 1, SEQ.ID.NO: 2 and SEQ.ID.NO:3. Particularly useful sets of primers include SEQ.ID.NO:1 as the forward primer and SEQ.ID.NO: 2 or SEQ.ID.NO: 3 as the reverse primer.

The present methods can also be used to distinguish between T-cell lymphomas and B-cell lymphomas. In these methods, canine IgH CDR-specific primers and canine T-cell receptor gamma-specific primers are used to obtain dominant and discrete DNA polymerase chain reaction products corresponding to B-cell and/or T-cell clonal rearrangements. Those skilled in the art can readily identify the appropriate combination of primers to be used in such methods.

Table 1 below provides a list of sequences for the primers that are particularly useful in the methods disclosed herein.

TABLE 1

Primer Sequences

| SEQ ID NO | SEQUENCE Description | SEQUENCE |
|---|---|---|
| 1 | DP1 Forward Ig | 5--CAG CCT GAG AGC CGA GGA CAC--3 |
| 2 | DP2 Reverse Ig | 5--TGA GGA GAC GGT GAC CAG GGT--3 |
| 3 | DP3v2 Reverse Ig | 5--TGA GGA CAC AAA GAG TGA GG--3 |
| 4 | DP4 Reverse TCRγ | 5--ACC TGA AGA ATT GTG CCA GG--3 |
| 5 | DP5 Reverse TCRγ | 5--GTT ACT ATA AAC CTG GTA AC--3 |
| 6 | DP6 Forward TCRγ | 5--TCT GGG A/GTG TAC/T TAC TGT GCT GTC TGG--3 |

TABLE 1-continued

Primer Sequences

| SEQ ID NO | SEQUENCE Description | SEQUENCE |
|---|---|---|
| 7 | Sigmf1 control Cμ | 5--TTC CCC CTC ATC ACC TGT GA--3 |
| 8 | Srmicron3 control Cμ | 5--GGT TGT TGA TTG CAC TGA GG--3 |

The sequences described in the sequence listing can be shortened from the 5' end, provided that the resulting sequence does not result in loss of specificity when the shortened sequence is used as a primer. The shortened primers are also useful as a part of a genus-specific primer set. For example, those primers having the 5' terminus shortened by 1–10 bases are also within the scope of the present invention. Primers having the 5' terminus shortened by 1–8 bases are also useful. Primers having 14 bases in length and include at least one differentiating codon can also be used.

Those skilled in the art can readily identify other canine IgH CDR3-specific and T-cell receptor gamma-specific primers useful in the present methods. Intergenic sequences of organisms are generally available through journal publications, or though Genbank or the NIH BLAST database. The most used database can be found on the internet at ncbi.nlm.nih.gov. A search for intergenic sequences would typically include searching on either a known sequence or the name of the organisms to be distinguished.

Moreover, it is known in the art that primers are preferably G-C rich, ideally more than 50% of the bases being G or C. The length of the primer is usually chosen to minimize the chances of amplifying non-target nucleic acid, as well as minimize self-hybridization. Primers are typically 17 to 30 bases in length, although there are no absolute rules with regard to length or G-C content. For the purposes of the present invention, other parameters may take precedent over the length or constitution of the primers. Certain computer programs (such as MacVector) are helpful in primer design and PCR condition optimization.

The methods disclosed herein include both a PCR step and an amplicon size-determination step. First, PCR can be conducted according to techniques known to those of skill in the art, including for example, thermocycle PCR and isothermal PCR. A number of printed publications describe these procedures. For instance Sambrook et al., *Molecular Cloning: A Laboratory Manual* (Cold Spring Harbor Laboratory Press, 1989); Ausubel et al., *Current Protocols in Molecular Biology* (Greene Publishing Associates, Inc., 1993); and Walker et al., 89 *Proc Natl Acad Sci USA* 392 (1992) describe typical procedures and parameters. Moreover, journal articles by investigators studying the organisms of interest will typically contain details about PCR amplification of the organisms' nucleic acid.

For example, thermocycle PCR can be conducted by first subjecting a test sample to amplification. Then, a thermocycler is used (at alternatingly high and low temperatures) to promote dissociation of double stranded nucleic acid, followed by hybridization of the primers to a nucleic acid in the test sample, and subsequent synthesis of complementary nucleic acid. When the primers are bound to a nucleic acid in the test sample, the polymerase synthesizes a nucleic acid complementary to the sample nucleic acid, and when the primers are not bound, no synthesis takes place.

A suitable test sample includes, but is not limited to, a bodily fluid composition or a cellular composition. A bodily fluid refers to any fluid that can be collected (i.e., obtained) from a canid or felid, examples of which include, but are not limited to, blood, plasma, urine, tears, aqueous humor, cerebrospinal fluid (CSF), saliva, lymph, nasal secretions, milk and feces. Aspirates of solid tissue, including those obtained via biopsy of tissue, are particularly useful.

The second step in the present methods is a size-determination of the PCR products generated. Size determination can be carried out according to any method known to those skilled in the art, including, for example, gel electrophoresis. Other size separation methods can also be used, including, for example, HPLC. Methods for determining size of PCR products are described in Sambrook, supra and Ausubel, supra. Use of a control (identity known) sample or a sizing ladder is particularly useful.

Those skilled in the art are aware that certain aspects of the invention can be altered by similar reagents or methods, so long as the goal is accomplished. For example, the source or nature of the specific reagents may change, the type of polymerase may change (the form of Taq may change, or other thermostable polymerases may be used), the thermocycler protocol may be altered in such a way as to accomplish amplification under different conditions, the method for separating products by size may be changed (e.g., HPLC or other methods may be utilized as long as identification of different products is possible), samples may be obtained, stored and used in different forms (e.g., fresh, frozen or paraffin samples may be used). In addition, changes in the the primer sequences may be possible as described above, provided appropriate amplification still takes place.

The present invention also provides kits containing components useful for performing the methods disclosed herein. Such kits preferably contain at least one set forward and reverse primers for use in the present methods. The kits can also contain control primers, such as primers having sequences identified as SEQ.ID.NO: 7 and SEQ.ID.NO: 8. The kits can further contain reagents and associated components for performing PCR and/or detecting clonal rearrangements. For example, the kit can include materials for gel electrophoresis, such as agarose or acrylamide.

The following Examples are intended to illustrate, but not limit, the present invention.

EXAMPLE 1
Detection Methods for Canine Malignancies
A. Selection of Cases

Criteria for entry into this study were definitive diagnosis of lymphoma, myeloma or lymphoid leukemia using histologic or cytologic criteria in the tissue examined or, definitive diagnosis of another condition with no evidence, clinical or physical, of lymphoid malignancy. Samples were obtained from several sources. First, immunophenotyped, definitively diagnosed leukemias were specifically sought from stored frozen tissue (University of California at Davis and Texas A&M University). Second, cases of lymphoma and leukemia from the Colorado State University (CSU) Veterinary Teaching Hospital were obtained as they presented to the clinic. A local reference lab was also contacted and agreed to provide leukemias for testing by PCR (only leukemias were available as fresh, rather than formalin fixed tissue). No attempt was made to distinguish acute from chronic lymphocytic leukemias. Non-lymphoid tumors and inflammatory conditions for which there was a definitive diagnosis were selected from samples obtained at CSU as part of other ongoing studies in the laboratory. Because the samples were not collected in a random fashion with respect to type of lymphoid neoplasm, no conclusions about the prevalence of different types of rearrangements can be made.

Samples were included only if neoplasia was detected histologically or cytologically in the tissue tested by PCR. For example if an animal had lymphoma involving a lymph node, but there was no evidence of disease in the bone marrow by cytology, the bone marrow sample was not used for this study even if a rearrangement was found in the marrow. In a few cases, animals presented with diseases that could be considered antecedent to the development of lymphoma (for example pancytopenia). These cases were only included if the animal was followed for at least 6 months without the development of lymphoma. Cases of suspected or confirmed myeloid or myelo-monocytic leukemia were not included for several reasons. First, often it can be difficult to determine the lineage of leukemic cells by cytology, and there is little consensus about the appropriate immunocytochemical markers to use for differentiating lymphoid from undifferentiated myeloid origin leukemias. Therefore it can be difficult to rule out the possibility of lymphoid origin in cells with rearrangements. In addition, in human patients, up to 40% of myeloid origin tumors can have antigen receptor rearrangements (Kyoda et al., *Leukemia*, 11:803–806 (1997)), making it possible that this assay will not be useful for differentiating lymphoid from myeloid leukemias.

All samples were read by board certified anatomic or clinical pathologists who were not aware of the PCR results. Most samples were tested by PCR after the diagnosis of neoplasia. All of the gels were read by another specialist who was not aware of the diagnosis for each sample.

B. Immunophenotyping

Samples from U.C. Davis were analyzed as described in Moore et al., *Adv Vet Derm* 3:77–94 (1998), incorporated herein by reference. Samples from Colorado State University (CSU) were typed as follows; antibody was added to 10 to 50 µl of whole blood in an amount suggested by the manufacturer and incubated at room temperature for 20 minutes in the dark. Antibodies used were anti-canine CD4, CD8a, CD45 and CD5 from Serotech (clones YKIX302.9, YCATE55.9, YKIX716.13, and YKIX322.3 respectively), anti-human CD14, HLA-DQ (class II major histocompatibility complex) and CD21 from Pharmingen (clones TUK4, TU169 and B-Iy4, respectively). Incubation was carried out in a 96 well plate. 150 µl of lysis buffer (0.15M $NH_4Cl$, 1M $KHCO_3$, 0.1 mM $Na_2EDTA$, 1N HCl to a pH of 7.2–7.4) was added to each well and incubated for 5 minutes at room temperature. The plate was spun for 2 minutes at 2000 rpm and the supernatant flicked out of the wells. If there was gross evidence of red cells remaining in the well, this process was repeated as many as two more times. A lineage (B or T) was only assigned to a neoplasm if it bound to one of the T cell antibodies (CD4, CD5 or CD8a) or the B cell antibody (CD21). It should be noted that while the anti-human CD21 cross reacts with canine lymphocytes, there is as yet no proof that it recognizes the homologous protein. In this study, no discrepancies were found between CD21 staining and the type of rearrangement present.

C. Identification of Primers for the Ig Reaction

Ig primers were identified in canine VH cDNA clones (Genbank accession # AF067449-AF067453). The cDNA clones were generated using 5'RACE (Zhang Y and Frohman, *Meth Mol Biol*, 69:61–87 (1997), incorporated herein by reference) from RNA derived from the spleen of a healthy dog. 3' anchor primers used for this methodology were designed according to the exon 1 sequence of canine Cmu [SRMu3: GGT TGT TGA TTG CAC TGA GG (SEQ.ID.NO:8); SRMu2 ATG TAC TCG TCT GAA CC (SEQ.ID.NO:9) and SRMu1 CAT TGG AGT GCT TGA CGT TG (SEQ.ID.NO:10)]. The sequence data was generated using heterologous primers to amplify cDNA from the peripheral blood of a healthy dog). cDNA was inserted into the T/A cloning vector pGEM-T (Promega). Five clones were sequenced, with all of these clones having V region framework 3 sequences containing a conserved region that could be amplified with a common primer (DP1). In these five samples, two clearly distinct J region sequences were identified. Primers for each gene were selected (DP2 and DP3v2). Therefore, for routine typing, a single primer V region primer was used, and two J region primers.

D. Identification of Primers for the T-cell Receptor (TCR) Reaction

Studies in the literature suggested that in humans, TCRγ rearrangements may be easier to detect, and a more sensitive measure of clonality, than TCRβ rearrangements, regardless of which gene is expressed by the tumor (Diss et al., *J Clin Pathol* 48:1045–1050 (1995); Theodorou et al., *J Path* 178:303–310 (1996); Theodorou et al., *J Path* 174:233–242 (1994), all incorporated herein by reference. Therefore, the TCRγδ locus was chosen as a means of identifying clonal T cell populations. TCRγ cDNA was obtained from the thymus of a healthy dog using a heterologous Vγ primers (hetvg3 & hetvg6) and a canine Cγ primer. The Vγ primers were designed based on a comparison of bovine and rabbit Vγ sequences. This comparison revealed high conservation at the 3' end of Vγ. This primer was used to generate V-J cDNA clones and in subsequent routine typing. Five V-J clones were sequenced (Genbank accession AF079118-079123) and again, two different J sequences were identified. Thus, as with the Ig genes, a single V region primer and two J region primers were used in routine typing.

E. PCR Conditions Used for Routine Typing

DNA samples are prepared with the QIAamp DNA mini kit from Qiagen. For each sample four PCR reactions were run; 1. Cmu (positive control), 2. IgH major, 3. IgH minor, 4. TCRγ. Ig major and minor are designated as such to represent the use of the two different J region primers. The Ig major primers amplified the majority of immunoglobulin gene rearrangements, and the Ig minor primers amplified a minority of these rearrangements. We found that these primers could not be combined in the same reaction. However, the three TCR primers could be mixed in the same tube. For amplification, HotStarTaq Master Mix Kit was used. ~100–500 ng of DNA was amplified with 200–400 nM each primer in a 50 μl reaction volume. The Cmu positive control primers were taken from the constant region gene of IgM. The primers used are given below.

Cmu Primers

```
Sigmf1
5--TTC CCC CTC ATC ACC TGT GA--3    (SEQ. ID. NO: 7)

Srm3
5--GGT TGT TGA TTG CAC TGA GG--3    (SEQ. ID. NO: 8)
```

Immunoglobulin Primers (Majority of Rearrangements)

```
DP1 5--CAG CCT GAG AGC CGA GGA CAC-3    (SEQ. ID. NO: 1) VH

DP2 5--TGA GGA GAC GGT GAC CAG GGT--3   (SEQ. ID. NO: 2) JH (major)
```

Immunoglobulin Primers (Minority of Rearrangements)

```
DP1    5--CAG CCT GAG AGC CGA GGA CAC-3   (SEQ. ID. NO: 1) VH

DP3v2  5--TGA GGA CAC AAA GAG TGA GG-3   (SEQ. ID. NO: 3) JH (minor)
```

TCRγ Primers (Use all three Together)

```
DP4 5--ACC CTG AGA ATT GTG CCA GG-3          (SEQ. ID. NO: 4) Jγ

DP5 5--GTT ACT ATA AAC CTG GTA AC-3          (SEQ. ID. NO: 5) Jγ

DP6 5--TCT GGG A/GTG TAC/T TAC TGT GCT GTC TGG-3   (SEQ. ID. NO: 6) Vγ
```

A Perkin-Elmer thermocycler 9600 was used for all experiments. Samples were initially heated to 95° F. for 15 min (conditions specific for the activation of HotStar Taq, Qiagen). The cycling profile was as follows; 94° F. for 8 seconds, 60° F. for 10 seconds and 72° F. for 15 seconds for 35 cycles. No final extension time was used. PCR products were analyzed on 10% native PAGE, (1.5 mm thick) with 1xTBE buffer. Bromophenol blue was run until the dye front had moved approximately 14 cm. The Cm product is approximately 130 base pairs (bp), the Ig products center around 120 bp and the TCR products center around 90 bp.

All samples that had discordant results (that is samples that were PCR+ but histologically negative for lymphoma, or PCR negative and histologically positive for lymphoma) were repeated. All samples gave precisely the same results when repeated. In addition, 24 other samples were randomly selected and repeated. Each gave the same result the second time.

EXAMPLE 2

Results

A. Detection of Gene Rearrangements Using a Panel of Lymphoid Neoplasms

Figure 1A:
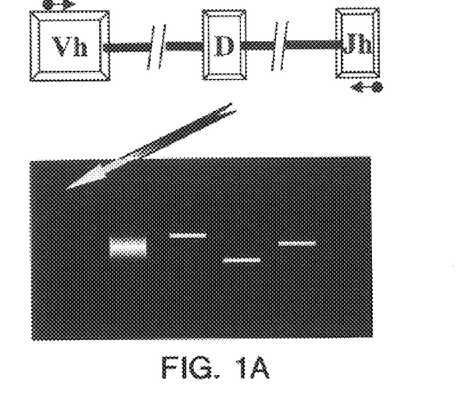
FIGS. 1A–1C show schematic representations of PCR results from non-lymphoid (FIG. 1A), normal lymphoid (FIG. 1B) and neoplastic lymphoid (FIG. 1C) tissue.
Figure 1B:
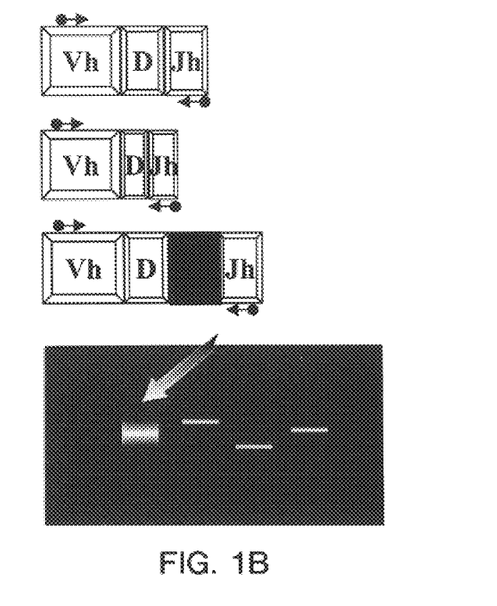
Figure 1C:
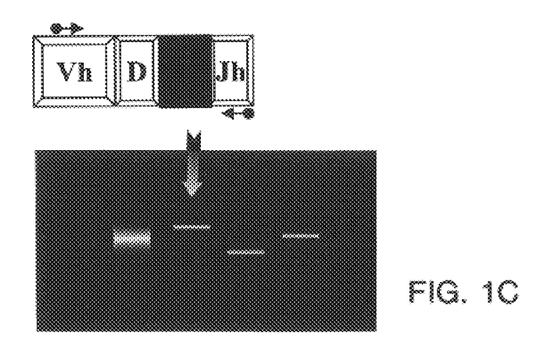
Figure 2A:
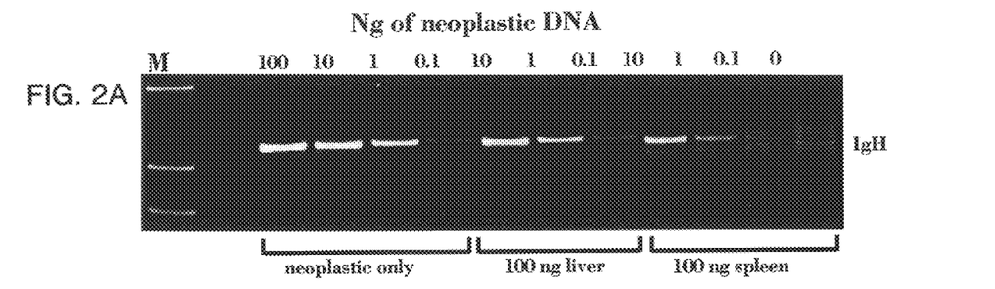
FIGS. 2A–2B show the sensitivity of detection of rearranged bands.
Figure 3A:
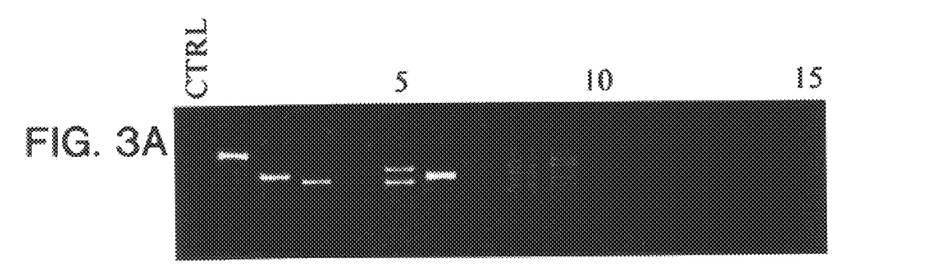
Figure 3B:
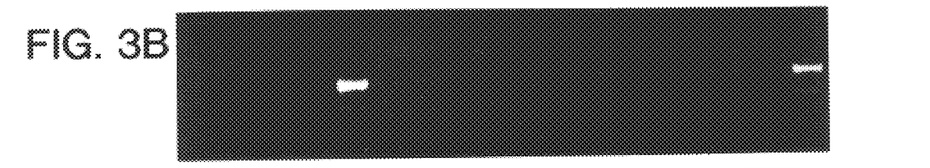
Figure 3C:
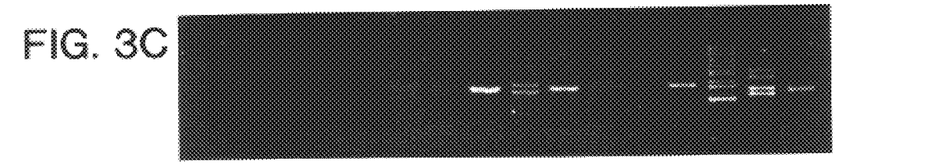
Figure 3D:
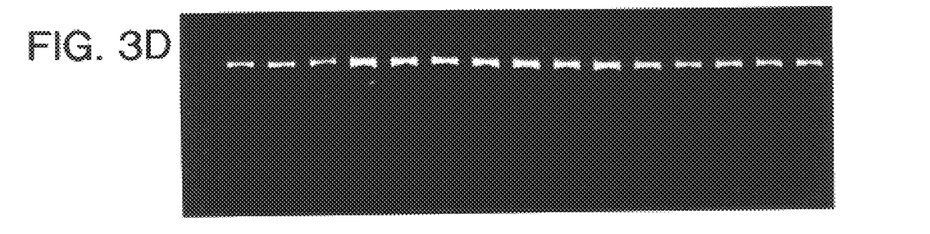

DNA was extracted from tissues taken from dogs with a variety of conditions as described in Example 1, and amplified with primers specific for Ig and TCR genes. Cmu primers were used to amplify each sample as a positive control for DNA, and a negative control (no DNA added) was also carried out for each reaction FIGS. 3A–3D show the amplification of DNA from 16 samples, chosen to represent the array of samples tested and the results obtained. All samples had sufficient DNA for analysis as shown by the consistent amplification of a product with the Cmu primers (FIG. 3D). The spectrum of results with the three different primer sets can be seen in FIGS. 3A–3C. The kinds of results obtained included a single detectable rearrangement of an Ig gene (lanes 1–4 and 6), a bi-clonal rearrangement of Ig genes (lane 5), or single (lanes 7, 9, 12), bi-clonal (lane 8) or oligoclonal (lanes 13 and 14) rearrangement of TCRγ genes. A single sample was found to have rearrangements in both Ig and TCRγ genes (lane 15). Negative results can appear as either no visible bands (lanes 10 and 11), or a ladder-like smear (lane 9, FIG. 2A—this dog had a TCR rearrangement on a background of normal B cells that gave rise to the smear with Ig primers). Generally, clonal rearrangements and the smear generated from normal lymphoid tissues have a 40 bp size range.

The source of material for each sample is listed in the Brief Description of the Drawings for FIGS. 3A–3D. Samples of all types, including biopsies, peripheral blood, bone marrow, cavity fluids and aspirates gave sufficient material for analysis. Material from aspirates had the greatest tendency to give insufficient DNA yield. It was found that in general, aspirating the site, such as a lymph node, at least three times into physiologic saline and rinsing the syringe each time in the saline would give sufficient material for analysis.

Results for all 72 animals are presented in Table 2, and a breakdown of the types of lymphoid neoplasms that were tested is shown in Table 3. A monoclonal, bi-clonal or oligoclonal pattern was found in 93% of all lymphoid malignancies tested (n=54). Only one sample (6% of the total tested) from a dog without a definitive diagnosis of lymphoma was found to have a T cell receptor gene rearrangement in a bone marrow sample. Using this population of dogs, the sensitivity of this assay was 93% and the specificity was 94%. It should be noted that the limited published (Ruslander et al., *In vivo,* 11:169–172 (1997) evaluation of canine leukemias has demonstrated that most leukemias are CD8+ T cell in origin, with a smaller number being B cell. In the present study, a greater number of B cells were tested than T cell leukemias, but this is the result of non-random case selection, not a reflection of the true distribution of the B and T cell phenotypes amongst leukemias.

TABLE 2

Results of PCR analysis on a panel of lymphoid neoplasms and non-lymphoid conditions

|  | n | Ig−/TCR− | Ig+/TCR− | Ig−/TCR+ | Ig+/TCR+ |
|---|---|---|---|---|---|
| Lymphoid malignancies | 54 | 4 (7)* | 30 (56) | 19 (34) | 1 (2) |
| Non-lymphoid conditions** | 18 | 17 (94) | 0 | 1 (6) | 0 |

*Number in parentheses refers to percent of total.
**Non-lymphoid conditions included peripheral blood from dogs with the following diagnoses: healthy (2), immune mediated hemolytic anemia (2); aspirates or biopsies from the following conditions: mast cell tumors (6), rhinitis (1), malignant fibrous histiocytosis (1), perianal adenocarcinoma (1), meningitis (1), inflammation (1); bone marrow from dogs with the following conditions: pancytopenia (1), pure red cell aplasia (1). The TCR+ dog was diagnosed with ehrlichiosis. Lymphoid malignancies are detailed in Table 3.

TABLE 3

Breakdown of lymphoid malignancies

|  | n | Ig−/TCR− | Ig+/TCR− | Ig−/TCR+ | Ig+/TCR+ |
|---|---|---|---|---|---|
| Lymphoma | 20 | 3 (15)* | 10 (50) | 7 (35) | 0 |
| Lymphocytic leukemia** | 31 | 1 (3) | 17 (55) | 12 (39) | 1 (3) |
| Myeloma | 2 | 0 | 2 (100) | 0 | 0 |
| Plasmacytoma | 1 | 0 | 1 (100) | 0 | 0 |

*Number in parentheses refers to percent of total.
**All lymphocytic leukemias (chronic and acute) were grouped together.

Some of the leukemias in this study were immunophenotyped by flow cytometry. Only those cases in which a definitive phenotype (T versus B in origin) could be established were included in this part of the study. The myelomas and plasmacytoma were also included, even though they were not immunophenotyped, since these tumors are known to be of B cell lineage. The majority of cases were either not phenotyped, or did not react with any of the panel of antibodies tested. Concordance was found between the phenotype obtained by flow cytometry or immunohistochemistry and the rearrangement detected by PCR in all cases but one (Table 4). This suggests that the PCR method can be a useful adjunct to immunophenotyping. The exception would be in those rare cases (one in this study) where both types of rearrangements are identified.

TABLE 4

Rearrangement according to phenotype**

|  | n | Ig−/TCR− | Ig+/TCR− | Ig−/TCR+ | Ig+/TCR+ |
|---|---|---|---|---|---|
| T cell | 6 | 1 (17)* | 0 | 4 (66) | 1 (17) |
| B cell | 14 | 0 | 14 (100) | 0 | 0 |

*Number in parentheses refers to percent of total.
**Phenotype was established by flow cytometry or immunochemistry as described in the materials and methods. Myelomas and plasmacytomas were not immunophenotyped because they are presumed to be of B cell origin. Typing was not attempted in all cases. In some cases, phenotyping with the available markers did not yield a positive result (i.e. the neoplastic cells did not stain with any available markers) and were therefore not included.

B. Limits of Detection of Gene Rearrangements Within Different Tissues

Figure 2B:
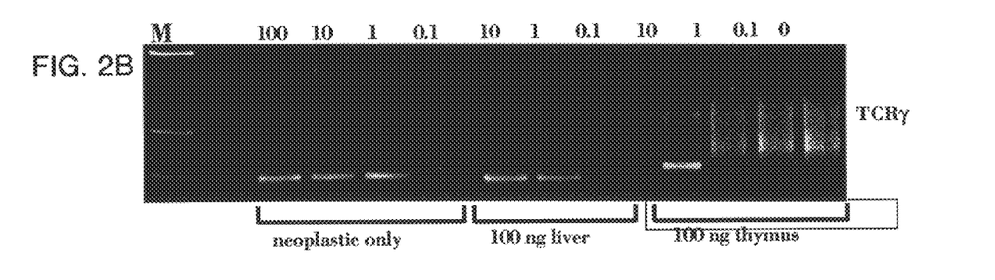

One use of this assay will be to establish the presence of lymphoid malignancy in tissue biopsies and bone marrow samples. Therefore, the sensitivity of the assay when used in a background of normal lymphoid or non-lymphoid tissue was determined. In order to measure sensitivity, DNA from a B cell leukemia which exhibited a clean, single band in the IgH PCR was diluted serially by 10 fold from 100 ng to 0.1 ng (FIGS. 2A–2B, lanes 1–4). A single rearrangement was still detectable when as little as 0.1 ng DNA was used. A similar result was seen when DNA from the leukemia was diluted into a constant amount of DNA extracted from normal liver (lanes 5–7) which demonstrates that in a non-lymphoid organ, this assay can detect a malignant clone which comprises as little as 0.1% of the tissue. When the same dilutions were performed in DNA from normal spleen (lanes 8–11), a clear dominant rearrangement was seen at 1 ng of DNA (representing 1% of the total DNA present), but this band was obscured by background bands at 0.1% of the total DNA. Comparable results were observed with TCRγ amplification except when diluted into DNA from the thymus, when the neoplastic band could only be seen at 10% of the input DNA. Thus, the nature of the tissue from which the sample is taken influences the sensitivity of the assay.

EXAMPLE 3

Detection Methods for Feline Malignancies

The methods described in Example 1, including the primers, were used to detect lymphoid malignancies in cats. Fourteen cats were tested, of these fourteen, six had serologically-confirmed lymphoid T-cell neoplasia, and five of the confirmed neoplastic cats were positive by the present PCR method. None of the neoplasia-free animals were positive when tested by the present PCR method.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method of detecting B-cell clonal rearrangement in a canine test sample, said method comprising the steps of:
   (a) conducting a polymerase chain reaction using starting materials which comprise a canine test sample and at least one set of IgH CDR3-specific primers having at least one forward and at least one reverse primer, wherein at least one forward primer comprises the sequence of SEQ.ID.NO:1; and
   (b) detecting B-cell clonal rearrangement in the test sample in the event one or more dominant and discrete DNA polymerase chain reaction products are present.

2. The method of claim 1, wherein the at least one reverse primer comprises the sequence set forth in SEQ.ID.NO:2 or SEQ.ID.NO:3.

3. The method of claim 2, wherein the at least one reverse primer comprises the sequence set forth in SEQ.ID.NO:2.

4. The method of claim 2, wherein the at least one reverse primer comprises the sequence set forth in SEQ.ID.NO:3.

5. A method of detecting B-cell clonal rearrangement in a canine test sample, said method comprising the steps of:
   (a) conducting a polymerase chain reaction using starting materials which comprise a canine test sample and at least one set of IgH CDR3-specific primers having at least one forward and at least one reverse primer, wherein the at least one reverse primer comprises a sequence selected from the group consisting of SEQ.ID.NO:2 and SEQ.ID.NO:3; and
   (b) detecting B-cell clonal rearrangement in the test sample in the event one or more dominant and discrete DNA polymerase chain reaction products are present.

6. A method of diagnosing a B-cell lymphoid malignancy is a canid, said method comprising the steps of:

(a) obtaining a test sample from the canid;
(b) conducting a polymerase chain reaction using starting materials which comprise the test sample obtained in step (a) and at least one set of IgH CDR3-specific primers having at least one forward and at least one reverse primer, wherein the at least one reverse primer comprises a sequence selected from the group consisting of SEQ. ID.NO:2 and SEQ.ID.NO:3; and
(c) detecting B-cell clonal rearrangement in the test sample in the event one or more dominant and discrete DNA polymerase chain reaction products are present, wherein the presence of said DNA polymerase reaction products is diagnostic of B-cell lymphoid malignancy in the canid.

7. The method of claim 6, wherein detecting the B-cell clonal rearrangement in step (c) is by gel electrophoresis.

8. The method of claim 6, wherein the at least one forward primer comprises the sequence of SEQ.ID.NO:1.

9. The method of claim 7, wherein at least one reverse primer comprises the sequence of SEQ.ID.NO:2.

10. The method of claim 7, wherein at least one reverse primer comprises the sequence of SEQ.ID.NO:3.

11. A method of diagnosing a T-cell lymphoid malignancy is a canid or a felid, said method comprising the steps of:
(a) obtaining a test sample from the canid or felid;
(b) conducting a polymerase chain reaction using starting materials which comprise the test sample obtained in step (a) and at least one set of T-cell receptor gamma-specific primers having at least one forward and at least one reverse primer, wherein the set of primers comprises the sequences set forth in SEQ.ID.NO:4, SEQ.ID.NO:5 and SEQ.ID.NO:6; and
(c) detecting T-cell clonal rearrangement in the test sample in the event one or more dominant and discrete DNA polymerase chain reaction products are present, wherein the presence of said DNA polymerase reaction products is diagnostic of T-cell lymphoid malignancy in the canid or felid.

12. The method of claim 11, wherein detecting the T-cell clonal rearrangement in step (c) is by gel electrophoresis.

13. A kit useful for detecting clonal rearrangement in a canine test sample comprising a canine or feline T-cell lymphoid malignancy, said kit comprising a set of primers, wherein the primers comprise the sequences set forth in SEQ.ID.NO: 4, SEQ.ID.NO:5 and SEQ.ID.NO:6.

14. The kit of claim 13, further comprising control primers comprising the sequences set forth in SEQ.ID.NO:7 and SEQ.ID.NO:8.

15. A kit useful for detecting clonal rearrangement in a canine test sample comprising a canine B-cell lymphoid malignancy, said kit comprising a set of primers, wherein the set of primers comprises at least one primer comprising a sequence from the group consisting of SEQ.ID.NO:1, SEQ.ID.NO:2 and SEQ.ID.NO:3 with the proviso that when the primer comprises the sequence set forth in SEQ ID NO:2, the kit further comprises a primer comprising a sequence selected from the group consisting of SEQ ID NO:1, SEQ ID NO:7, and SEQ ID NO:8.

16. The kit of claim 15 comprising a primer comprising the sequence set fourth in SEQ ID NO:2 and further comprising control primers comprising the sequences set forth in SEQ.ID.NO:7 and SEQ.ID.NO:8.

17. A method of distinguishing B-cell and T-cell lymphoid malignancy in a canine test sample, said method comprising the steps of:
(a) conducting a polymerase chain reaction using starting materials which comprise a canine test sample and at least two sets of primers, wherein each set of primers have at least one forward primer and at least one reverse primer, wherein the sets of primers comprise at least one set of primers comprising at least one sequence selected from the group of IgH CDR3-specific primers selected from the group of SEQ ID NO:1, SEQ ID NO:2 and SEQ ID NO:3, and at least one set of primers comprising the T-cell receptor gamma-specific sequences given in SEQ.ID.NO:4, SEQ.ID.NO:5 and SEQ.ID.NO:6; and
(b) detecting clonal arrangements in the test sample in the event one or more dominant and discrete DNA polymerase chain reaction products are present.

18. The kit of claim 15 wherein the set of primers comprises nucleotide sequences comprising SEQ ID NO:1 and SEQ ID NO:2.

19. The kit of claim 18, further comprising a primer comprising the sequence set forth in SEQ ID NO:7 and primer comprising the sequence set forth in SEQ ID NO:8.

20. The kit of claim 15 wherein the set of primers comprises nucleotide sequences comprising SEQ ID NO:1 and SEQ ID NO:3.

21. The kit of claim 20 wherein the set of primers comprises nucleotide sequences comprising SEQ ID NO:7 and SEQ ID NO:8.

22. The kit of claim 15 comprising a primer comprising the sequence set forth in SEQ ID NO:3 and control primers comprising the sequences set forth in SEQ ID NO:7 and SEQ ID NO:8.

* * * * *

UNITED STATES PATENT AND TRADEMARK OFFICE
CERTIFICATE OF CORRECTION

PATENT NO. : 6,596,492 B2 Page 1 of 1
DATED : July 22, 2003
INVENTOR(S) : Avery et al.

It is certified that error appears in the above-identified patent and that said Letters Patent is hereby corrected as shown below:

<u>Title page</u>,
Item [57], ABSTRACT,
Line 6, delete "caninen" and replace with -- canine --.

<u>Column 3</u>,
Line 48, insert -- be -- between "to" and "defined".

<u>Column 4</u>,
Line 51, delete "product" and replace with -- products --.
Line 52, delete "lympid" and replace with -- lymphoid --.

<u>Column 8</u>,
Line 57, insert -- of -- between "set" and "forward"

<u>Column 18</u>,
Line 67, delete "is" and replace with -- in --.

<u>Column 19</u>,
Line 24, delete "is" and replace with -- in --.
Line 43, delete "canine"

Signed and Sealed this

Twentieth Day of April, 2004

JON W. DUDAS
*Acting Director of the United States Patent and Trademark Office*

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
cagcctgaga gccgaggaca c                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
tgaggagacg gtgaccaggg t                                              21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
tgaggacaca aagagtgagg                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
accctgagaa ttgtgccagg                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
gttactataa acctggtaac                                                20

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer
<223> OTHER INFORMATION: At position 7, r = a or g
<223> OTHER INFORMATION: At position 12, y = c or t -continued

```
<400> SEQUENCE: 6
tctgggrtgt aytactgtgc tgtctgg                                         27

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 7
ttccccctca tcacctgtga                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 8
ggttgttgat tgcactgagg                                                 20

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 9
atgtactcgt ctgaacc                                                    17

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 10
cattggagtg cttgacgttg                                                 20
```